United States Patent [19]

Batchelor et al.

[11] Patent Number: 4,461,907

[45] Date of Patent: Jul. 24, 1984

[54] AMINO-SUBSTITUTED FLAVANS USEFUL AS ANTI-VIRAL AGENTS

[76] Inventors: John F. Batchelor, 10, Wilton Pl., Overbury Ave., Beckenham, Kent; Denis J. Bauer, 80 Clifton Hill, St. John's Wood, London NW8; Harold F. Hodson, 69 Whitecroft Way, Park Langley, Beckenham, Kent; John W. T. Selway, Westcroft, Hartley La., Cranbrook, Kent; David A. B. Young, 47, Sylvan Way, West Wickham, Kent, all of England

[21] Appl. No.: 398,211

[22] Filed: Jul. 14, 1982

Related U.S. Application Data

[63] Continuation-in-part of Ser. No. 127,465, Mar. 5, 1980, abandoned, which is a continuation-in-part of Ser. No. 20,256, Mar. 14, 1979, abandoned.

[30] Foreign Application Priority Data

Mar. 15, 1978 [GB] United Kingdom ............... 10251/78

[51] Int. Cl.[3] ............................................ C07D 311/60

[52] U.S. Cl. .................................... 549/406; 549/404; 424/283

[58] Field of Search ................................ 549/404, 406

[56] References Cited

U.S. PATENT DOCUMENTS 3,450,717 6/1969 Krämer et al. ....................... 549/406

OTHER PUBLICATIONS

Terrell et al., J. Antimicrob. Chemo., 9, 340 (1982).

*Primary Examiner*—Nicky Chan

*Attorney, Agent, or Firm*—Donald Brown

[57] ABSTRACT

Novel compounds of formula (IID)

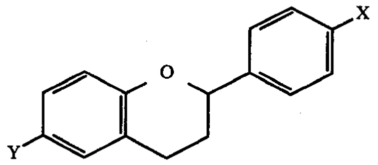

wherein either both X and Y represent groups independently selected from amino and lower alkylamino, or one of X and Y represents a group selected from amino and lower alkylamino and the other of X and Y represents a hydrogen atom have been found to be active against rhinoviruses and other viruses. Processes for producing these compounds include reduction of flavanone derivatives or of flavenes. Alternatively, reductive cyclization of chalcones affords the compounds. These may also be prepared by condensation of o-(substituted methyl)phenols with styrene derivatives.

Pharmaceutical formulations and methods for the administration of the compounds are described.

6 Claims, No Drawings

AMINO-SUBSTITUTED FLAVANS USEFUL AS ANTI-VIRAL AGENTS

PRIOR APPLICATION

This application is a Continuation-in-part of Application Ser. No. 127,465 filed Mar. 5, 1980, now abandoned; which is in turn a c.i.p. of Application Ser. No. 020,256 filed Mar. 14, 1979, now abandoned.

This invention relates to anti-viral agents, particularly compounds and pharmaceutical formulations having activity against rhinoviruses.

Rhinoviral infections are responsible for about 70% of cases when the disease generally known as the common cold is experienced, although infections by other viruses such as entero- and coronaviruses and allergic reactions may also result in 'colds'. Mankind throughout the world is prone to rhinoviral infection, which is a major cause of sickness and absence from work and therefore of great economic significance.

The common cold is transmitted via droplets exhaled when an infected person coughs or sneezes, which are then inhaled by another and initiate infection of the respiratory tract. After an incubation period of from 48 hours to two weeks the infected person may suffer from a sore throat, coughing, sneezing, increased mucous secretions and fever due to secondary bacterial infection.

Some resistance to a rhinovirus serotype remains after infection but does not confer immunity to other serotypes. Continual re-infection by serotypes prevalent in a particular community maintains a level of resistance to these viruses in most individuals. A cold is consequently experienced only when a new serotype is encountered, on average 2 to 3 times a year.

Since there is no cross-immunity and there are at least 120 known immunologically distinct rhinovirus serotypes, vaccination is not a viable method of treatment. As a method of reducing the incidence of colds, air hygiene has been tried but was unsuccessful. It appears that the only practical treatment would be a compound which is suitable for administration to humans and active against preferably all common serotypes or at least a wide range of rhinoviruses. Despite considerable research effort, such compounds have not been forthcoming to date, and there is no established chemotherapeutic agent against the disease.

It has now been found that flavan and various derivatives thereof are active against certain viruses including those which infect the respiratory tract, and for instance, picorna, menge-, arbo-, myxo-, corona-, herpes- and adenovirus. In particular these compounds have activity against rhinoviruses, especially against serotypes 1B, 2 and 9. Apart from some compounds falling into this class, which are known but have not been reported to have any relevant activity in this respect, further novel derivatives have also been prepared and tested. It was observed that these compounds can inhibit rhinoviruses during in vitro tests in culture and some also show some activity against other viruses such as herpes, influenza and measels viruses. Additionally, the same compounds have in vivo activity against rhinoviruses, in particular when administered at appropriate dosages, in humans and other mammals. Whilst flavan itself has quite good activity against rhinoviruses, substituted derivatives have similar or enhanced activity, depending on the nature and position of the substituent.

The compounds have also been shown to have very low toxicity, with $LD_{50}$ in excess of 500 mg/kg.

Activity may be detected by the plaque inhibition test and measured by the plaque reduction test. Both assays involve the formation of a monolayer cell culture in a petri dish followed by infection with a virus suspension, and then overlaying the culture with nutrient agarose in the form of a gel. This gel ensures that there is no spread of virus throughout the culture and thus areas of localised cell destruction or plaques are formed.

In the plaque inhibition test a filter paper disc which holds 0.01 ml when impregnated with a solution of compound is placed on top of the agarose gel. The compound may then diffuse throughout the gel so that its greatest concentration will be around the disc and its lowest concentration towards the periphery of the petri dish. The efficacy of the compound may be detected by observing the zone of inhibition of plaque formation.

Detectable activity is measured with the plaque reduction assay. A range of concentrations of compound of known molarity are incorporated in the nutrient agarose overlay. Plaque suppression is proportional to compound concentration. Plaque numbers are expressed as percentages of a control, and a dose response curve may be drawn. From this curve 50% of the effective dose (ED50) may be estimated.

Some flavans are already known in the chemical literature, but no public disclosure has been made to suggest their use for treatment of the human or animal body except for 3,3',4,4',5,7-hexahydroxy flavan which may be used to treat venous disorders, -3-hydroxy flavan which was tried without success against viral hepatitis (Lancet;2;1153 (1977)); various 3,6-dialkyl or dialkoxyl flavans (U.S. Pat. No. 3,555,047) which may lower blood cholesterol levels; 1-epi-3',4',5',5,7-pentahydroxy flavan-3-ol (J. M. Gazave; Fruits; 32; 275–284; (1977)), a potential antiscorbutic agent and 3,3',4',5,7-pentahydroxy flavan (French Pat. Nos. 988332 and 988333) which may have a vitamin-like effect on blood capillaries According to the present invention, therefore, there is provided flavan or a derivative thereof having a general formula (I), (I)

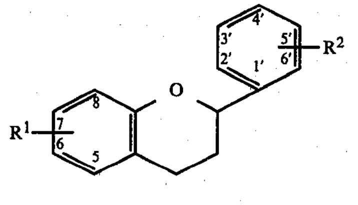

or, where appropriate a pharmaceutically acceptable salt thereof, wherein $R^1$ and $R^2$ represent substituents selected from the class set out hereinbelow, for the purpose of preventing or treating viral infections. Alternatively a compound of formula (I) is provided in a pharmaceutical composition in association with a pharmaceutically acceptable carrier or excipient.

In formula (I), $R^1$ may represent hydrogen or up to 4 substitutents and $R^2$ may represent hydrogen or up to 5 substituents. It is preferred that $R^1$ and $R^2$ each represent up to 2 substituents and most preferably $R^1$ and $R^2$ each represent one substituent.

Preferably the compound has substituents $R^1$ at the 6 or 7 positions and/or $R^2$ at the 2',3',4', 5' or 6' positions, the 6 and 4' positions being particularly preferred. It has also been found that the size of the substituent may be relevant. For instance, in the 4' and 6 positions, enhanced activity is associated with a substituent having an $[R]_D$ value below 15, preferably below 10.

The $[R]_D$ value is a corrected molar volume as described in S. Glasstone, Text-book of Physical Chemistry, 2nd Edn. 1948, MacMillan, London, Pg. 528. It may be calculated from the molar mass, M, density $\rho$ and refractive index, $\eta$, according to the equation:

$$[R]_D = \frac{M}{\rho} \times \frac{n^2 - 1}{n^2 + 2}$$

Values for many substituents have been determined by Vogel and published in *J. Chem. Soc.* throughout the year 1948.

Advantageously, substituents may be halogen atoms or nitro, cyano, trifluoromethyl, lower alkyl, lower alkoxyl, lower alkylamino, amino or hydroxyl groups. Chloro, nitro, cyano and hydroxyl groups are preferred and chlorine is the most preferred substituent.

Conditions of selection of number, position and kind of substituent can conveniently be combined so as to increase the likelihood of enhancement of activity. However, the ultimate properties of the compounds in use are also dependant on other physical and biological characteristics.

According to the present invention in another aspect there is provided a compound of the general formula (II), (II)

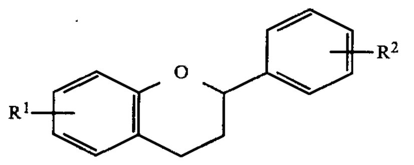

or where appropriate a pharmaceutical acceptable salt thereof wherein either or both $R^1$ and $R^2$ represent one or more substitutents selected from the class comprising halogen atoms, or nitro, cyano, trifluoromethyl, lower alkyl, lower alkoxyl, amino, lower alkylamino or hydroxyl groups provided that either (a) the compound is monosubstituted and that substituent is other than a 4'-,5-, or 7-methoxyl, 6-methyl, 6-amino or 7-hydroxyl group; or (b) the compound is monosubstituted with respect to $R^1$ and monosubstituted with respect to $R^2$ the two substituents being other than 4'-methoxyl group together with a 6- or 7-methoxyl or 7-hydroxyl group or a 4'-hydroxyl group together with a 7-methyl or 7-hydroxyl group; or (c) the compound is disubstituted with respect to either $R^1$ or $R^2$ and the other is unsubstituted, the two substituents being other than 5,7-dimethyl or 5, 7-dihydroxyl, 5-methoxyl-7-hydroxyl, 6-butyl-7-hydroxyl or 3',4'-dimethoxyl or dihydroxyl groups; or (d) the compound is tri- or tetrasubstituted, the substituents being other than 5,7-dimethoxyl combined with either 4'-methoxyl, or 3',4'-dihydroxyl or 3',4'-dimethoxyl, or 4',6-dihydroxyl or else 4'7-dimethoxyl together with either 3'- or 6-methoxyl or else 5-hydroxyl-4-methoxyl together with 7-hydroxyl or 7-methoxyl or else 5,6,7,8,-tetrachloro substituents.

Salts of compound (I) or (II) may be formed when there is a hydroxyl or amino substituent. Pharmaceutically acceptable salts are those of mineral acids such as hydrochloric or sulphuric acid, organic acids such as lactic, maleic, and acetic acid, and of bases as sodium or potassium.

Compounds within the above class may carry substituents in accordance with the preferences stated hereinabove in relation to formula (I).

Thus it is preferred that compounds confirm to formula (II')

(II')

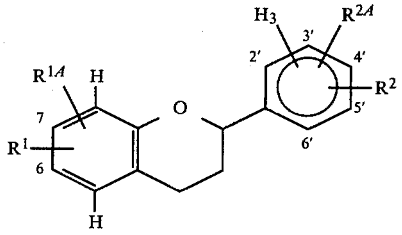

wherein (a) $R^1$ is selected from the class consisting of halogen, nitro, cyano, trifluoromethyl and lower alkylamino, $R^{1A}$ is selected from the class consisting of halogen, nitro, cyano, trifluoromethyl, lower alkylamino, lower alkyl and hydrogen, $R^2$ and $R^{2A}$ are the same or different and are selected from the class consisting of halogen, nitro, cyano, trifluoromethyl, lower alkylamino, amino, lower alkyl, 2'-, 3'-, 5'- and 6'-lower alkoxyl, 2'-, 3'-, 5'- and 6'-hydroxyl and hydrogen;

or (b) $R^1$ and $R^{1A}$ are the same or different and are selected from the class consisting of hydrogen and lower alkyl $R^2$ is selected from the class consisting of halogen, nitro, cyano, trifluoromethyl, loweralkylamino, amino, lower alkyl, 2'-, 3'-, 5'- and 6'-lower alkoxyl and 2'-, 3'-, 5'- and 6'-hydroxyl and $R^{2A}$ is selected from the class consisting of halogen, nitro, cyano, trifluoromethyl, loweralkylamino, amino, lower alkyl, 2'-, 3'-, 5'- and 6'-lower alkoxyl, 2'-, 3'-, 5'- and 6'-hydroxyl and hydrogen and wherein however at least one of $R^1$, $R^{1A}$, $R^2$ and $R^{2A}$ is hydrogen.

Within this group of compounds, those corresponding to formula (IIA)

(IIA)

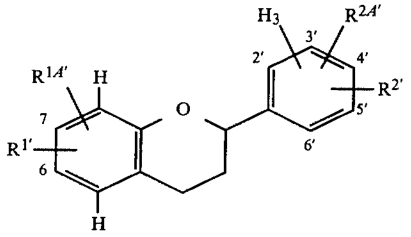

wherein (a) $R^{1'}$ is selected from the class consisting of halogen and cyano, $R^{1A'}$ is selected from the class consisting of halogen, cyano and hydrogen, $R^{2'}$ and $R^{2A'}$ are the same or different and are selected from the class consisting of halogen, cyano, amino, lower alkyl, 2'-, 3'-, 5'- and 6'-lower alkoxyl, 2'-, 3'-, 5'- and 6'-hydroxyl and hydrogen, or (b) $R^{1'}$ and $R^{1A'}$ are hydrogen, $R^{2'}$ is selected from the class consisting of halogen, cyano, amino, lower alkyl, 2'-, 3'-, 5'- and 6'-lower alkoxyl and 2'-, 3'-, 5'- and 6'-hydroxyl, and $R^{2A'}$ is selected from the class consisting of halogen, cyano, amino, lower alkyl, 2'-, 3'-, 5'- and 6'-lower alkoxyl, 2'-, 3'-, 5'- and 6'-hydroxyl and hydrogen, and wherein however at least one of $R^{1'}$, $R^{1A'}$, $R^{2'}$ and $R^{2A'}$ is hydrogen, to formula (IIB)

(IIB)

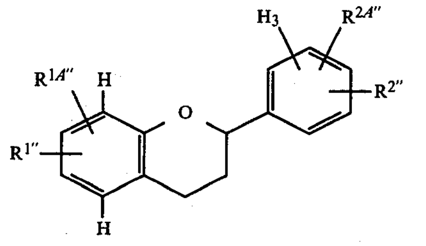

wherein (a) $R^{1''}$ is selected from the class consisting of halogen, nitro, cyano, trifluoromethyl and lower alkylamino, $R^{1A''}$ is selected from the class consisting of halogen, nitro, cyano, trifluoromethyl, lower alkylamino, lower alkyl and hydrogen. $R^{2''}$ and $R^{2A''}$ are the same or different and are selected from the class consisting of halogen, nitro, cyano, trifluoromethyl, lower alkylamino, amino, lower alkoxyl, 2'-, 3'-, 5'- and 6'-lower alkyl, 2'-, 3'-, 5'- and 6'-hydroxyl and hydrogen, or (b) $R^{1''}$ and $R^{1A''}$ are the same or different and are selected from the class consisting of hydrogen and lower alkyl, $R^{2''}$ is selected from the class consisting of halogen, nitro, cyano, trifluoromethyl, lower alkylamino, amino, lower alkyl, 2'-, 3'-, 5'- 6'-lower alkoxyl and 2'-, 3'-, 5'- and 6'-hydroxyl, and $R^{2A''}$ is selected from the class consisting of halogen, nitro, cyano, trifluoromethyl, loweralkylamino, amino, lower alkyl, 2'-, 3'-, 5'- and 6'-lower alkoxyl, 2'-, 3'-, 5'- and 6'-hydroxyl and hydrogen, and wherein however two of $R^{1''}$, $R^{1A''}$, $R^{2''}$ and $R^{2A''}$ are hydrogen;

and to formula (IIC)

(IIC)

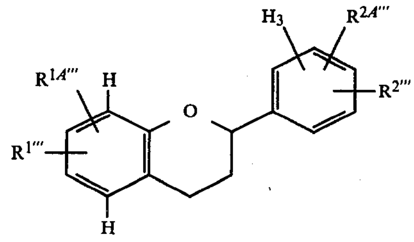

wherein (a) $R^{1'''}$ is selected from the class consisting of halogen, nitro, cyano, trifluoromethyl and lower alkylamino, $R^{1A'''}$ is selected from the class consisting of halogen, nitro, cyano, trifluoromethyl, lower alkylamino, lower alkyl and hydrogen, $R^{2'''}$ and $R^{2A'''}$ are the same or different and are selected from the class consisting of halogen, nitro, cyano, trifluoromethyl, lower alkylamino, amino, lower alkoxyl, 2'-, 3'-, 5'- and 6'-lower alkoxyl, 2'-, 3'-, 5'- and 6'-hydroxyl and hydrogen or (b) $R^{1'''}$ and $R^{1A'''}$ are the same or different and are selected from the class consisting of hydrogen and lower alkyl $R^{2'''}$ is selected from the class consisting of halogen, nitro, cyano, trifluoromethyl, loweralkylamino, amino, lower alkyl, 2'-, 3'-, 5'- and 6'-lower alkoxyl and 2'-, 3'-, 5'- and 6'- hydroxyl, and $R^{2A'''}$ is selected from the class consisting of halogen, nitro, cyano, trifluoromethyl, loweralkylamino, amino, lower alkyl, 2'-, 3'- 5'- and 6'-lower alkoxyl, 2'-, 3'-, 5'- and 6'-hydroxyl and hydrogen, and wherein however at least one of $R^{1'''}$, $R^{1A'''}$, $R^{2'''}$ and $R^{2A'''}$ is hydrogen and wherein any substituent at the 4' or 6 position has an $[R]_D$ value below about 15, are more preferred.

The novel compounds having the highest activity in tests are 4'-fluoro-flavan,3'-4'-dichloro-6-methyl flavan,4'-chloro-7-methyl-flavan, 6-chloro-4'-methoxyl-flavan, 6-methoxyl-flavan, 4'-methyl-flavan,6-chloro-4'-methyl-flavan and 4', 6-dichloro-flavan, 6-chloro-4'-fluoro-flavan, 6-iodo-4'-chloroflavan, 6-fluoro-4'-chloroflavan, 6-fluoro-4'-bromoflavan, 4',6-dibromo-flavan, 6-cyano-4'-chloroflavan, 4',6-dicyanoflavan.

According to the present invention in a further aspect there is provided a process for producing compounds of formula (I) or (II) comprising either (a) the reduction by methods known per se of a compound of formula (III)

(III)

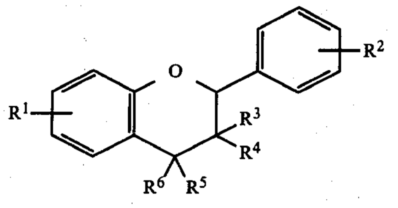

wherein $R^1$ and $R^2$ are as hereinbefore defined with respect to formula (I) or (II) and either $R^3$ and $R^6$ are hydrogen atoms and $R^4$ and $R^5$ are the same or different and are hydrogen or halogen atoms or hydroxyl groups provided that only one of $R^4$ and $R^5$ is a hydrogen atom, or $R^4$ and $R^5$ together form a double bond or one of the geminal pairs $R^3$ and $R^4$ or $R^5$ and $R^6$ represents an oxo-, ketal, thioketal or dithioketal group and one of the other pair is a hydrogen atom, and the other is a hydrogen or halogen atom or a hydroxyl group, or a tautomer or salt thereof; or (b) the sequential reduction then cyclisation or cyclisation then reduction by methods known per se of a compound of formula (IV) with or without isolation of intermediate products, (IV)

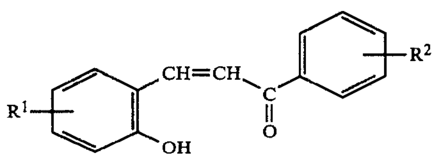

wherein $R^1$ and $R^2$ are as defined in (a) above; or (c) the condensation by methods known per se of a compound of formula (V)

(V)

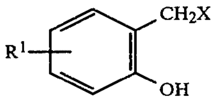

wherein $R^1$ is as defined in (a) above, and X is a hydroxyl group or a halogen atom, with a compound of formula (VI)

(VI)

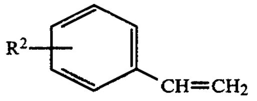

wherein $R^2$ is as defined in (a) above; and optionally thereafter converting a compound of formula (I) or (II) so formed into another compound of formula (I) or (II) by methods known per se and if required forming salts of compounds of formula (I) or (II) by reaction of the compound having an amino or hydroxyl substituent, in an aqueous medium, with an appropriate mineral or organic acid or base.

There is a variety of well known techniques available for use in method (a) such as the Clemmensen and Wolff Kischner reductions, or catalytic hydrogenation using such catalysts as palladium charcoal, copper chromium oxide or Raney nickel.

The Clemmensen reduction (e.g. E. L. Martin, *Organic Reactions,* (1942) 1, 161) and variations of this technique (e.g. E. Vedej's, *Organic Reactions* (1974), 22, 412; B. L. Verma, et al, *Indian J. Chem,* (1962) 3 (12), 565; M. M. Bokadia & B. L. Verma, *Chem. and Ind.* (1964), 235)) are particularly convenient for reducing ketone derivatives of formula (III).

The Wolff Kischner reduction is only applicable to compounds of formula (III) wherein $R^3$ and $R^4$ together represent an oxo group. This reaction involves the formation of the hydrazone derivative of the ketone, which intermediate is then reduced.

Reduction of dithioketals may be achieved by, for example, the use of Raney nickel in dioxan (E. J. Keogh, et al, *Chem. and Ind.* (1961) 2100)

Flavanone may also be reduced using lithium aluminium hydride mixed with aluminium chlorides (M M Bokadia et al, *J. Chem. Soc.* (1962) 1658; B. L. Verma et al, *Indian J. Chem.* (1965) 3(12) 565).

The flav-3-ene derivatives of formula (III) are conveniently reduced used sodium borohydride or other complex hydride reagents (J. W. Clark-Lewis and R. W. Jemison, *Austral. J. Chem.* (1968) 21, 2247).

Catalytic reductions of compounds of formula (III), particularly the halogenated derivatives, may be effected by equivalent techniques to those described by J. W. Clark-Lewis (above), M. Suzuki et al, *Nippon Kagaku Zasshi* (1968) 89(9), 878–82 and (1969) 90(4), 397–400 and R. Mozingo and H. Adkins, *J. Am. Chem. Soc.,* (1938) 60, 669.

In method (b), compounds of formula (IV) can be cyclised by treatment with hydrochloric acid, affording the flavyllium salt, which may be reduced to a flavan by catalytic hydrogenation (e.g. U.S. Pat. No. 3,555,047).

The chalcone may be reduced to the dihydrochalone by catalytic hydrogenation. The required flavan is then obtained by treatment of the dihydrochalcone with zinc chloride in benzene (e.g. Van Allan, Reynolds and Regan, *J. Org. Chem,* (1967) 32, 1897). Alternatively the chalcone may be treated with a complex hydride reducing agent, such as sodium borohydride or cyanoborohydride, to provide the corresponding (2-hydroxyphenyl-)ethylphenylcarbinol. The latter is then cyclised using an acid catalyst such as acetic or p-toluenesulphonic acid (e.g. L. Jurd, *Chem. and Ind.* (1967) 2175).

Combined reduction and cyclisation of chalcones of formula (IV) is effected when these compounds are treated with a mixture of lithium aluminium hydride and aluminium chloride (M. M. Bokadia et al, *J. Chem. Soc.* (1962), 1658).

In method (c) condensation may be effected thermally or, in the case of those compounds wherein X is a halogen atom, by using a Friedel Crafts type catalyst in a suitable solvent. In this case, stannic chloride is the preferred catalyst and 1,2 dichloro ethane is the preferred solvent. The products may be obtained by distillation in the case of low boiling flavan derivatives, especially after thermal condensation, or by chromatography where appropriate. Alternatively the condensation may occur in the presence of an acid, especially sulphuric acid (e.g. R. R. Schmidt, *Tet. Letters,* (1969), 60, 5279; K. Hultzsch, *J. prakt. Chem.* (1941), 158, 275; M. Wakselman and M. Vilkas, C.R. hebd. Séances, Acad. Sci. (1964) 258, 1526).

It has been found particularly convenient to synthesise flavan and derivatives thereof by Clemmensen reduction of flavanones of formula (III) wherein $R^3$ and $R^4$ are hydrogen and $R^5$ and $R^6$ together represent an oxo-group, or by catalytic reduction of a flav-3-ene of formula (III) wherein $R^4$ and $R^5$ together from a double bond using palladium charcoal in a suitable solvent such as an alcohol, e.g. ethanol, or a lower carboxylic acid, e.g. acetic acid, or an aromatic solvent such as toluene.

Flav-3-enes are preferably obtained by treatment of the corresponding 2'-hydroxy chalcone with a complex hydride, preferably sodium borohydride.

Reduction and cyclisation according to method (b) is most preferably performed by treating the compound of formula (IV) with a sodium borohydride in an ether solvent, preferably tetrahydrofuran, followed by cyclisation using a suitable acid, preferably acetic acid.

Condensation according to method (c) is most preferably performed by heating the compounds of formula (V) and (VI) at a temperatures between 150° and 250° C.

Compounds of formula (III) above may be prepared by acid or base catalysed cyclisation of chalcones of formula (VII)

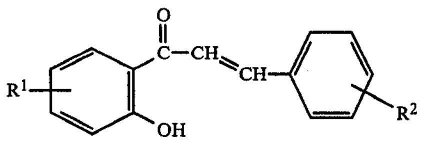

(VII)

wherein $R^1$ and $R^2$ are as defined in (a) above. These chalcones, and those of formula (IV) above are prepared by Knoevenagel condensation of appropriately substituted acetophenone and benzaldehyde derivatives (Nielsen, *Organic Reactions,* (1968), 16, 44). This may occur by acid or base catalysis in aqueous or organic media using either organic or inorganic acids or bases such as alkali metal hydroxides or alkoxides.

The starting materials and intermediates described above and the acetophenone and benzaldehyde derivatives required to prepare chalcones (IV) and (VII) are commercially available or may be prepared by methods known per se (see for instance refs. cited above).

In a further aspect, the present invention provides a pharmaceutical composition comprising a compound of formula (I) or (II), a tautomer of pharmaceutically acceptable salt thereof together with a pharmaceutically acceptable carrier therefor. In a particular aspect the pharmaceutical composition comprises a compound of formula (I) or (II) in effective unit dose form.

As used herein the term "effective unit dose" is denoted to mean a predetermined antiviral amount sufficient to be effective against the viral organisms in vivo. Pharmaceutically acceptably carriers are materials known and accepted for the purpose of administering the medicament, and may be solid, liquid or gaseous materials, which are otherwise inert and medically acceptable and are compatible with the active ingredients.

These pharmaceutical compositions may be given parenterally, orally, or intranasally, or used as a suppository, as an inhaler, ointment, cream, aerosol, powder, or vapour or given as nose drops etc., when the preparation is used to treat rhinoviral infections.

For such infections the compositions are administered orally or parenterally at dose levels, calculated as the free flavan, of about 0.125 μg to 1.25 mg per kg, preferably 0.25 μg to 0.125 mg/kg, most preferably 0.8 to 300 μg/kg of mammal body weight and are used in a unit dosage form, administered a few times daily in the amount of 10 μg to 100 mg conveniently 0.1 to 10 mg per unit dose.

For such infections the compositions are administered orally or parenterally at close levels, calculated as the free flavan, of about 0.125 μg to 1.25 mg/kg, preferably 0.25 μg to 0.125 mg/kg, most preferably 0.8 to 30 μg/kg of mammal body weight. Suitably, dosages of about 5 μg/kg body weight are administered to humans. Such compositions are conveniently administered in a unit dosage form given a few times daily in the amount of 10 μg to 100 mg, conveniently 0.1 to 10 mg, preferably about 0.3 to 3 mg and most preferably about 1 mg per unit dose. For humans a suitable dosage regime is from 1 to 10 mg in equally divided doses three times per day.

For oral administration, fine powders or granules may contain diluting, dispersing and/or surface active agents, and may be presented in a draught, in water or in a syrup; in capsules or sachets in the dry state or in a non-aqueous solution or suspension, wherein suspending agents may be included; in tablets, wherein binders and lubricants may be included; or in a suspension in water or a syrup. Where desirable or necessary, flavouring, preserving, suspending, thickening or emulsifying agents may be included. Tablets, capsules and granules are preferred, and these may be coated. Alternatively, the compositions are administered as a solution of the compound of formula (I) or (II) in an appropriate oil based medium The compositions may also be administered intranasally using inhalers, aerosols or sprays or by inhalation of a vapour containing the compound of formula (I) or (II).

For parenteral administration, or for administration as aerosols, sprays or drops, the compounds may be presented in aqueous solution in a concentration of from about 0.1 to 10%, more preferably 0.1 to 1%, most preferably 0.2% w/v. The solution may contain antioxidants, buffers, etc.

In yet a further aspect of the invention there is provided a method of treating viral infections in mammals as hereinbefore defined, of a compound of formula (I) or (II) or where appropriate a pharmaceutically acceptable salt thereof. Administration is preferably by the oral, intranasal or parenteral route.

The invention will now be illustrated with reference to the following Examples, which are not intended to limit the scope of the invention in any way.

EXAMPLE 1-47

Preparation of chalcone intermediates

Substituted benzaldehydes for use in the following Examples were obtained commercially.

O-Hydroxyacetophenone for use in the following examples was obtained commercially substituted derivatives thereof were prepared by Fries rearrangement of the corresponding phenylacetate derivative or by other literature methods.

EXAMPLE 1

Preparation of 2'-hydroxy-5'-methylchalcone

To a solution of 2-hydroxy-5-methylacetophenone (30.0 g) and benzaldehyde (21.2 g.) in ethanol (250 ml.) was added a solution of potassium hydroxide pellets (39.5 g) in water (100 ml.)

The resulting clear solution was allowed to stand for 4 hrs. at room temperature, during which time it turned red. It was poured on to ice and concentrated hydrochloric acid (80 ml), and the precipitated yellow chalcone filtered off, washed with water and recrystallised from ethanol to yield $2^1$-hydroxy-$5^1$-methylchalcone (31 g) as orange crystals (m.p. 107°-108° C.).

EXAMPLE 2 TO 44

The compounds of Examples 2 to 44 were prepared by a method exactly analogous to that employed in Example 1, using appropriately substituted starting materials.

| EXAMPLE | COMPOUND | m.p. (°C.) |
|---|---|---|
| 2 | 2'Hydroxychalcone | 89-90 |
| 3 | 2-chloro-2'-hydroxy-chalcone | 98-100 |
| 4 | 3-Chloro-2'-hydroxy-chalcone | 105-106 |
| 5 | 4-Chloro-2'-hydroxy-chalcone | 152-153 |
| 6 | 3,4-Dichloro-2'- | 155-157 |

-continued

| EXAMPLE | COMPOUND | m.p. (°C.) |
|---|---|---|
| | hydroxychalcone | |
| 7 | 2,4-Dichloro-2'-hydroxychalcone | 169–171 |
| 8 | 2,6-Dichloro-2'-hydroxychalcone | 100–104 |
| 9 | 4-Bromo-2'-hydroxychalcone | 144–146 |
| 10 | 4-Fluoro-2'-hydroxychalcone | 110–113 |
| 11 | 2'-Hydroxy-2-methylchalcone | 77–79 |
| 12 | 2'-Hydroxy-3-methylchalcone | Oil-not characterised |
| 13 | 2'-Hydroxy-4-methylchalcone | 119–120 |
| 14 | 2,2'-Dihydroxychalcone | 160–161 |
| 15 | 2',4-Dihydroxychalcone | 160–161 |
| 16 | 2'-Hydroxy-2-methoxychalcone | 110–112 |
| 17 | 2'-Hydroxy-3-methoxychalcone | 94–96 |
| 18 | 2'-Hydroxy-4-methoxychalcone | 94–95 |
| 19 | 2'-Hydroxy-4-(N,N—dimethylamino) chalcone | 175–177 |
| 20 | 2'-Hydroxy-4-acetylaminochalcone | 198–202 |
| 21 | 4'-Chloro-2'-hydroxychalcone | 124–126 |
| 22 | 4,4'-Dichloro-2'-hydroxychalcone | 160–162 |
| 23 | 4'-Chloro-2'-hydroxy-4-methoxychalcone | 140–142 |
| 24 | 4'-Chloro-2'-hydroxy-4-methylchalcone | 160–162 |
| 25 | 5'-Chloro-2'-hydroxychalcone | 108–109 |
| 26 | 4,5'-Dichloro-2'-hydroxychalcone | 190–193 |
| 27 | 5'-Chloro-2'-hydroxy-4-methylchalcone | 131–133 |
| 28 | 5'-Chloro-2'-hydroxy-4-methoxychalcone | 107–109 |
| 29 | 5'-Chloro-2'-hydroxy-4-bromochalcone | 192–194 |
| 30 | 4-Chloro-2'-hydroxy-5'-methylchalcone | 150 |
| 31 | 3,4-Dichloro-2'-hydroxy-5'-methylchalcone | not characterised |
| 32 | 2'-Hydroxy-4,5'-dimethylchalcone | 104–109 |
| 33 | 2'-Hydroxy-4-methoxy-5'-methylchalcone | 96 |
| 34 | 5'-Fluoro-2'-hydroxychalcone | 85–96 |
| 35 | 5'-bromo-2'-hydroxychalcone | 108–109 |
| 36 | 5'-bromo-2'-hydroxy-4-methylchalcone | 119–120 |
| 37 | 5'-bromo-4-chloro-2'-hydroxychalcone | 188–190 |
| 38 | 3',4-dichloro-2'-hydroxychalcone | 108–109 |
| 39 | 2'-hydroxychalcone | 86–88 |
| 40 | 2'-hydroxy-4-isopropylchalcone | 93–95 |
| 41 | 5'-Chloro-2'-hydroxy-4-isopropylchalcone | 93–95 |
| 42 | 5'-ethyl-2-hydroxychalcone | (not obtained pure) |
| 43 | 4-Chloro-5'-ethyl-2'-hydroxychalcone | 89–90 |

EXAMPLE 44

Preparation of 5-Bromo-2-hydroxy-4'-methoxychalcone

5-Bromosalicylaldehyde (20.1 g) and p-methoxyacetophenone (15.0 g) were dissolved in ethanol (80 ml) and a solution of potassium hydroxide (26.5 g) in water (40 ml) was added, with cooling. The reaction mixture was allowed to stand overnight, and then was acidified by addition to excess hydrochloric acid. The precipitated 5-bromo-2-hydroxy.4'-methoxychalcone was filtered off, washed with water, and recrystallised from ethanol, 27.5 g, m.p. 177°–179°.

EXAMPLES 45 to 47

The compounds of Examples 45 to 47 were prepared by a method exactly analogous to that employed in Example 44, using appropriately substituted starting materials.

| EXAMPLE | COMPOUND | m.p. (°C.) |
|---|---|---|
| 45 | 2-Hydroxychalcone, | 153–154 |
| 46 | 2-Hydroxy-4'-methoxychalcone, | 144–146 |
| 47 | 2,4'-Dimethyl-2-hydroxychalcone, | 122–123 |

EXAMPLE 48–98

Preparation of Flavans from chalcones of Examples 1–47

EXAMPLE 48

Preparation of 4'-methylflavan

The 2'-Hydroxy-4-methylchalcone of Example 13 (7.3 g.) was boiled under reflux with a solution of 85% phosphoric acid (22 ml.) in 2-methoxyethanol (219 ml.) for 8 hrs. The reaction mixture was diluted with water (1 liter) and the oily precipitate extracted into dichloromethane (300 ml.). The organic extract was separated and washed with water and saturated sodium bicarbonate solution. Filtration and evaporation gave a residue of 4'-methylflavanone contaminated with the starting chalcone.

The intermediate flavanone could not be isolated in a pure form, because the chalcone-flavanone conversion is an equilibrium and seldom goes to completion or allows the flavanone to be separated easily from the generally less soluble chalcone. Therefore the Clemmensen reduction was carried out on the crude chalcone-flavanone mixture and reliance placed on alumina chromatography to remove phenolic impurities thus formed.

The crude flavanone was dissolved in a mixture of acetic acid (200 ml.) and concentrated hydrochloric acid (45 ml.), warmed to 50° C., and added to wet zinc amalgam (prepared from 60 g. zinc powder and 6 g. mercuric acetate). The mixture was swirled for 15 mins., allowed to stand for 30 mins., then heated on the steam bath for 15 mins. The residual zinc was filtered off and the filtrate diluted with water. The crude product was extracted into toluene and the extract washed with water and saturated sodium bicarbonate solution. Evaporation gave a residue which was chromatographed on alkaline, alumina, eluting with toluene. The first fraction obtained on evaporation of the solvent was recrystallised from ethanol to yield 4'-methylflavan (1.4 g.). m.p. 94° C.

EXAMPLES 49 TO 64

The compounds of Examples 49 to 64 were prepared by a method exactly anologous to that employed in Example 48 using the appropriate chalcone of Example 1 to 47

| EXAMPLE | COMPOUND | m.p. (°C.) |
|---|---|---|
| 49 | 7-Chloroflavan | 37-40 |
| 50 | 6-Chloro-4'-methyl-flavan | 132-134 |
| 51 | 4',6-Dichloroflavan | 97-99 |
| 52 | 6-Chloro-4'-methoxy-flavan | 83-84 |
| 53 | 4',6-Dimethylflavan | 90-91 |
| 54 | 4'-Methoxy-6-methyl-flavan | 57 |
| 55 | 4',7-Dichloroflavan | 62-65 |
| 56 | 7-Chloro-4'-methyl-flavan | 77-78 |
| 57 | 4'-Chloro-6-methylflavan | 89 |
| 58 | 3',4'-Dichloro-flavan | 76 |
| 59 | 7-Chloro-4'-methoxyflavan | 84 |
| 50 | 2',4'-Dichloro-flavan | B. pt. 138-142* |
| 61 | 2',6'-Dichloroflavan | 87-89 |
| 62 | 4'-Bromoflavan | 78-79 |
| 63 | 2'-Methylflavan | 73-75 |
| 64 | 3',4'-Dichloro-6-methylflavan | B. pt. 170-180** |

*at 0.05 mm Hg = 6.7 Pa
**at 0.15 mm Hg = 20 Pa.

EXAMPLE 65

Preparation of 4'-chloroflavan

4-Chloro-2'-hydroxychalcone (5.17 g) was boiled under reflux with a mixture of ethanol (250 ml.) and a solution or sodium acetate (anhydrous, 4.10 g) in water (25 ml.) for 5 hrs. The reaction mixture was diluted with water and allowed to stand overnight. The solid precipitate was filtered off, washed with water and dried. Recrystallisation from petroleum ether (b.p. 80°-100° C.) gave 4'-chloroflavanone (1.50 g.), m.p. 96°-98° C.

4'-Chloroflavanone (4.0 g.) was dissolved in acetic acid (150 ml.) and concentrated hydrochloric acid (20 ml.) and added to wet zinc amalgam (prepared from zinc powder (80 g.) and mercuric chloride (6.4 g.)). The reaction mixture was stirred for 1 hr. then allowed to stand overnight. The residual zinc was filtered off and washed with water, and the filtrate and washings combined and diluted with water. The oily product was extracted into ether, and the extract washed with water and saturated sodium bicarbonate solution; it was dried with magnesium sulphate, filtered and evaporated, and the residue chromatographed on alkaline alumina, eluting with toluene. The eluate was evaporated and the residue recrystallised from ethanol, to give 4'-chloroflavan, m.p. 76°-77° C.

EXAMPLES 66 TO 76

The compounds of Examples 66 to 76 were prepared by a method exactly analogous to that employed in Example 65 using the appropriate chalcones of Examples 1 to 47

| EXAMPLE | COMPOUND | m.p. (°C.) |
|---|---|---|
| 66 | 4'-methoxyflavanone | 90-91 |
| | 4'-methoxyflavan | 80-81 |
| 67 | 2'-chloroflavanone | 100-102 |
| | 2'-chloroflavan | b.p. 130-135° C./* |
| 68 | 3'-chloroflavanone | 100-102 |
| | 3'-chloroflavan | b.p. 120-125°/ |
| 69 | 3'-methoxyflavanone | 75-76 |
| | 3'-methoxyflavan | 53-55 |
| 70 | 4'-fluoroflavanone | 79-80 |
| | 4'-flouroflavan | 66-67 |
| 71 | 4'-bromo-6-chloro-flavanone | 154-155 |
| | 4'-bromo-6-chloro-flavan | 105-107 |
| 72 | 6-fluoroflavanone | 72-74 |
| | 6-fluoro flavan | 66-68 |
| 73 | 6-bromo flavanone | 118-120 |
| | 6-bromo flavan | 58-59 |
| 74 | 6-bromo-4'-methyl-flavanone | 116-119 |
| | 6-bromo-4'-methylflavan | 129-130 |
| 75 | 6-bromo-4'-chloro-flavanone | 155-157 |
| | 6-bromo-4'-chloro-flavan | 78-81 |
| 76 | Flavanone | 75-76 |
| | Flavan | 43-44. |

*at 0.1 mm Hg = 13.3 Pa.
at 0.07 mm Hg = 9.3 Pa.

EXAMPLES 77 TO 80

The compounds of Examples 77-80 were prepared by a method exactly analogous to that employed in Example 65 using the appropriate chalcones of Examples 1 to 47 except that the intermediate flavan one was not purified.

| EXAMPLE | COMPOUNDS | m.p. (°C.) |
|---|---|---|
| 77 | 2'-methoxyflavan | 80-81 |
| 78 | 3'-trifluoromethyl-flavan | 64-65 |
| 79 | 6-methoxyflavan | 85-86 |
| 80 | 4',8-dichloro-flavan | b.p. 137-142* |

*at 0.06 mm Hg = 8 Pa

EXAMPLES 81 AND 82

The compounds of Examples 81 and 82 were prepared by a method exactly analogous to that of Example 77 except that purification was by chromatography on Silica gel, eluted by the specified solvent, as opposed to alumina.

| EXAMPLE | COMPOUND | m.p. (°C.) |
|---|---|---|
| 81 | 4'-hydroxyflavan (dichloromethane) | 97-98 |
| 82 | 2'-hydroxyflavan (1:1 toluene: dichloromethane) | b.p. 130-135* |

*at 0.45 mm Hg = 60 Pa

EXAMPLE 83

Preparation of 6-chloroflavan

5'-Chloro-2'-hydroxychalcone (25.0 g) was dissolved in ethanol (125 ml.) and and aqueous solution of 1.5% sodium hydroxide (375 ml.) was added. The mixture was stirred at room temperature for 4 hrs. and the solid filtered off, washed with water and dried to give 6-chloroflavanone (16.65. g), mp. 90°–93° C. A sample recrystallised from 60°–80° C. petroleum ether had m.pt 95°–96° C. The flavanone (4.0 g) was dissolved in acetic acid (160 ml.) and concentrated hydrochloric acid (20 ml.) and added to amalgamated zinc (from zinc dust (40 g.) and mercuric chloride (0.5 g). The mixture was stirred for 1 hr., and allowed to stand overnight. The residual zinc was filtered off, and the filtrate diluted with water. The oily precipitate was extracted into either and the extract washed with water and saturated sodium bicarbonate solution, dried over magnesium sulphate, filtered and evaporated. The residue was chromatographed on alkaline alumina, eluting with 60°–80° C. petroleum either, to give 6-chloroflavan (0.52 g.), m.p. 71°–72° C.

EXAMPLES 84 TO 85

The compounds of Examples 84 and 85 were prepared by a method exactly analogous to that employed in Example 83 except that in Example 85 the flavanone intermediate was not characterised.

| EXAMPLE | COMPOUND | b.p. (°C.) |
|---|---|---|
| 84 | 6-methylflavan | 138–148* |
| | 6-methylflavanone | m.p. 107 |
| 85 | 3'-methylflavan | 114–120 |

*at 0.5 mm Hg = 67 Pa.
at 0.1 mm Hg = 13 Pa.

EXAMPLE 86

Preparation of 4'-(N,N-dimethylamino)flavan 4-(N,N-dimethylamino)-2'-hydroxychalcone (6.6 g.) was boiled under reflux with 2-N hydrochloric acid (100 ml.) for 3 hrs. The resulting solution of 4'-(N,N-dimethylamino) flavanone hydrochloride was added to a suspension of amalgamated zinc (from zinc powder (40 g.) and mercuric chloride (0.8 g.)) in water 30 ml. and the mixture stirred at 45° C. for 45 min. The residual zinc was separated by decantation from the aqueous liquor, stirred with acetic acid (150 ml.) and filtered. The zinc was further washed with acetic acid and the combined washing and filtrate were diluted with water and extracted with toluene. The extract was washed with water, dried over magnesium sulphate, filtered and evaporated. The residue was chromatographed on neutral alumina and the first fraction evaporated to give crystalline 4'-(N,N-dimethylamino) flavan which was recrystallised from methanol, and then 60°–80° C. petroleum ether, 0.7 g., m.p. 77°–78° C.

EXAMPLE 87

Preparation of 4'-aminoflavan

4-Acetylamino-2'-hydroxychalcone (7.20 g.), was boiled under reflux with acetic acid (100 ml) and concentrated hydrochloric acid (25 ml.) for 7 hrs. The clear solution of 4'-aminoflavanone hydrochloride was treated under a nitrogen atmosphere with amalgamated zinc (from zinc powder (40 g.) and mercuric chloride (0.8 g.)) and stirred at room temperature for 4 hrs. The residual zinc was filtered off and washed with acetic acid. The combined washings and filtrate were neutralised to bicarbonate solution, and the oily product extracted into dichloromethane. The solution was chromatographed on neutral alumina, eluting with dichloromethane and the first fraction evaporated giving the solid 4'-aminoflavan, which was recrystallised from boiling 60°–80° C. petroleum ether, cooling to −10° C., yielding 180 mg., m.p. 85°–87° C.

EXAMPLE 88

Preparation of flavan

2'-Hydroxychalcone (9.0 g) was stirred with ethanol (100 ml) at room temperature whilst sodium borohydride (3.05 g) was added in small portions. After 2 hr. stirring the colourless solution was evaporated to dryness and acetic acid (100 ml) added. Toluene sulphonic acid (1.0 g) was added and the solution was heated on the steam bath for 30 min. The solution was diluted with water and extracted with toluene. The extract was washed with saturated sodium bicarbonate solution, dried over magnesium sulphate, and evaporated. The residue was chromatographed on neutral alumina to yield flav-3-ene (6.3 g) as an oil, identified by its n.m.r. spectrum. The multiplet at 5.8 p.p.m. is characteristic of flav-3-enes.

The flav-3-ene was catalytically hydrogenated in acetic acid (60 ml) using 10% palladium carbon catalyst (150 mg) at room temperature and a atmospheric pressure. 750 ml hydrogen was absorbed over 3 hr. The reaction mixture was filtered, diluted with water, extracted with toluene, and the evaporated extract chromatographed on neutral alumina, eluting with toluene. The product was recrystallised from ethanol yielding flavan (2.75 g) m.pt. 43°–44° C.

EXAMPLES 89

Preparation of 4',6-Dichloroflavan 4,5'-Dichloro-2'-hydroxychalcone (7.32 g) was dissolved in ethanol (100 ml) and sodium borohydride (1.89 g) added in small portions. The reaction mixture was stirred for 1 hr at room temperature, evaporated to dryness, and diluted with water. The precipitated solid was filtered off, washed with water, and heated with acetic acid (100 ml) on the steam bath for 2 hr. The acetic acid was evaporated the residue dissolved in dichloromethane, and the solution washed sequentially with water, saturated sodium bicarbonate solution, and water, dried and evaporated. The residue was chromatographed on alumina, eluting with toluene, to give 4',6-dichloroflav-3-ene (3.84 g) as a colourless oil, identified by n.m.r. spectroscopy.

The flavene (3.7 g) was dissolved in acetic acid (100 ml), 10% palladium on carbon catalyst (100 mg) added, and the solution hydrogenated at room temperature and atomspheric pressure. After 1 hr, 400 ml. hydrogen had been taken up. The solution was filtered, diluted with water, and extracted with toluene. The extract was washed with water and saturated sodium bicarbonate solution, dried and evaporated. Recrystallisation of the residue gave 4',6-dichloroflavan (2.70 g) m.pt. 99°–100° C.

EXAMPLES 90 TO 93

The compounds of Examples 90 to 93 were prepared by a method exactly analogous to that of Example 80 from the appropriate compounds of Example 44 to 47

| EXAMPLE | COMPOUND | m.p. (°C.) |
|---|---|---|
| 90 | 4'-isopropylflavan | 46-47 |
| 91 | 6-chloro 4'- | 117-119 |

-continued

| EXAMPLE | COMPOUND | m.p. (°C.) |
|---|---|---|
| | isopropylflavan | |
| 92 | 6-ethylflavan | b.p. 130–140* |
| 93 | 4'-chloro-6-ethyl-flavan | 61–63 |

*at 0.15 mm Hg = 20 Pa

EXAMPLE 94

Preparation of flavan

2-Hydroxychalcone (28.5 g) was stirred with ethanol (500 ml) whilst sodium borohydride (9.45 g) was added in small portions. The solution, which turned from red to pale yellow was allowed to stand overnight at room temperature, then the solvent was evaporated off and the residue extracted with dichloromethane, washing with water. Evaporation of the solvent yielded 3-(o-hydroxyphenyl)-1-phenylpropan-1-ol (24.4 g). 1.0 g of this carbinol was dissolved in concentrated sulphuric acid, and the solution was allowed to stand at room temperature for 2 hr. The solution was poured into iced water, and the sticky orange product filtered off, washed with water, dried, and chromatographed on alumina, eluting with toluene. Evaporation of the eluate gave flavan (0.20 g), which was recrystallised from petroleum ether, b.p. 40°–60°, to give flavan m.p. 42°–43°.

EXAMPLE 95

Preparation of 4'-Methoxyflavan

2-Hydroxy-4'-methoxychalcone (12.7 g) was stirred with ethanol (200 ml) and sodium borohydride (3.8 g) added in portions. The solution was stirred at room temperature, the solvent evaporated, and the residue washed with water and recrystallised from aqueous ethanol to give 3-(o-hydroxyphenyl)-1-(p-methoxyphenyl)propan-1-ol (8.60 g), m.p. 114°–116°. The total product was boiled under reflux with acetic acid (100 ml) for 2 hr., the solution evaporated, and the residue chromatographed on alumina, eluting with toluene, to yield 4'-methoxyflavan (8.0 g), m.p. 82°–83°.

EXAMPLE 96

Preparation of 6-Bromo-4'-methoxyflavan

5-Bromo-2-hydroxy-4'-methoxychalcone (16.7 g) was suspended in ethanol (200 ml) and sodium borohydride (3.78 g) added in portions. The resulting solution was stirred for 30 min, then allowed to stand overnight. The solvent was evaporated off, and the residue dissolved in chloroform and washed with water. Evaporation of the solvent gave the crude carbinol intermediate which was boiled under reflux with acetic acid for 2 hr. On cooling, 6-bromo-4'-methoxyflavan crystallised out and was filtered off and dried, 10.2 g, m.p. 121°–123°.

EXAMPLE 97

Preparation of 2',4'-Dimethylflavan

2-Hydroxy-2',4'-dimethylchalcone (8.20 g) was suspended in ethanol (150 ml) and sodium borohydride (2.50 g) was added in portions. The mixture was stirred for 30 min and the resulting solution allowed to stand overnight. The solvent was distilled off and the residue dissolved in chloroform and washed with water. Evaporation of the chloroform gave the crude intermediate carbinol which was boiled under reflux with acetic acid (100 ml) for 2 hr. Evaporation gave an oily residue which was chromatographed on alumina, eluting with toluene. The main fraction, on evaporation of the solvent, was distilled under vacuum to give 2',4'-dimethylflavan, 4.80 g, b.p. 135°–145°/0.8 mm. Hg=107 Pa.

EXAMPLE 98

Preparation of 4',5,7-Trihydroxyflavan

4',5,7-Trihydroxyflavanone (10.5 g) was stirred with acetic anhydride (50 ml) and sulphuric acid (5 drops) for 2 hr at room temperature, then poured into iced water. The product was extracted into ether and the extracted washed with water, followed by sodium bicarbonate solution. 4',5,7-Triacetoxyflavanone was obtained on evaporation of the ether, and this was dissolved in a mixture of tetrahydrofuran (250 ml) and ethanol (250 ml). Sodium borohydride (1.2 g) was added over 5 min, and the solution stirred for 30 min. Further borohydride (1.8 g) was then added and stirring continued for a further 30 min. The solution was acidifed by cautious addition of glacial acetic acid (8 ml). The solvent was evaporated off and the residual oil extracted into chloroform, washed with water, dried and evaporated.

The residue was boiled, under reflux, with a mixture of ethanol (360 ml), water (240 ml) and imidazole (3.0 g) for 12 hr under nitrogen, the solution acidified with acetic acid (4.0 ml) and evaporated to dryness. The residue was extracted into chloroform (2×250 ml), the extract evaporated, and the residue chromatographed on silica gel, eluting with chloroform-methanol 95:5 to yield 0.9 g. of 4',5,7-trihydroxyflavan, m.p. 212°–215° C., (215°–217° C. on recrystallisation from acetic acid)

EXAMPLE 99

Preparation of 4'-(2-hydroxyethoxy) flavan

4'-Hydroxyflavan (2.26 g.), ethylene carbonate (8.8 g.) and tetramethylammonium iodide (0.30 g.) were heated together at 140° C. for 4 hrs. Sodium hydroxide (6.5 g) in water (20 ml.) and ethanol (250 ml.) was added, and the solution boiled under reflux for 5 hrs. The solution was filtered, diluted with water, and extracted 3 times with ether. The combined extracts were dried and evaporated, and the residue chromatographed on neutral alumina. The product was eluted with chloroform and after evaporation of the solvent was recrystallised from 60°–80° C. petroleum ether to yield 4'-(2-hydroxyethoxy) flavan (1.2 g.) m.p. 84°–85° C.

EXAMPLE 100

Preparation of 6,8-Dichloroflavan

A mixture of 2,4-dichlorophenol (15.3 g), 10% sodium hydroxide solution (100 ml) and 40% aqueous formaldehyde solution (37.5 ml) was heated at 95°–100° C. for 4 hr, then cooled and acidified by addition of 2-normal sulphuric acid (70 ml). The precipitated oil was extracted into toluene, and the extract washed with sodium bicarbonate solution, dried and evaporated. The residue was recrystallised from boiling water to yield 3,5-dichloro-2-hydroxybenzyl alcohol (4.0 g), m.p. 81°–82° C. on drying at 56° C./20 mm. Hg=2660 Pa.

3,5-Dichloro-2-hydroxybenzyl alcohol (4.0 g) and styrene (2.19 g) were heated together at 190° C. for 3 hr. The required 6,8-dichloroflavan was obtained on chromatography of the crude reaction mixture on alumina, eluting with toluene-petroleum ether (b.p. 60°–80° C.)

1:1, and recrystallised from petroleum ether (b.p. 60°-80° C.) to yield 2.60 g, m.p. 74°-76° C.

EXAMPLE 101

Preparation of 8-Chloroflavan

3-Chloro-2-hydroxybenzyl alcohol was prepared by the method of Zinate et al. J. Prakt. Chem. [2] (152) (1939) 126. The alcohol (3.96 g) was heated with styrene (2.6 g) at 180° C. for 2 hr., and the reaction mixture chromatographed an aluminia, eluting with toluene. The oil thus obtained on evaporation of the eluate was distilled under vacuum to yield 8-chloroflavan (0.12 g) b.pt. 155°-160° C./0.08 mm. Hg=10.7 Pa.

EXAMPLE 102

Preparation of Flavan

2-Hydroxybenzyl alcohol (15 g.) and styrene (75 g.) were heated together under reflux at 230° C. for 1.5 hrs. Distillation gave a forerun of styrene followed by flavan (13.9 g.) which was recrystallised from ethanol yeilding 10.3 g., m.pt. 44°-46° C.

EXAMPLE 103

In vivo testing

The compound 4',6-dichloroflavan was dissolved in olive oil B.P. at concentrations of 3 mg/ml and 1 mg/ml.0.1 ml aliquots of these solutions were administered to mice by the oral route.

Retro-orbital bleedings were performed at half, an hour, and 1 hour after administration of the dose, and hourly thereafter to 7 hours, and again at 24 hours. The plasma was harvested from these bleedings and was tested for antiviral activity using the plaque inhibition test described above. The total faeces of each mouse were collected after 24 hours and were macerated with a minimum of absolute alcohol, which liquid was then tested for antiviral activity by the plaque inhibition test. The gall bladders of the mice were removed and each was extracted with 10 μl of absolute alcohol, which extract was also tested by the plaque inhibition test.

Antiviral activity was observed in the plasma samples until 2 hours after administration, in the gall bladder and faeces extracts. By calibration against a standard curve, plasma concentrations after 1 hour were estimated at 2 to 4 μM for mice which received the lower dose, and at 10 μM for mice which received the higher dose (doses being approximately 30 mg/kg and 100 mg/kg body weight respectively).

EXAMPLE 104

Intranasal Administration—Simulation in vitro

Petri dishes were prepared, as for the plaque inhibition test and the confluent sheet of cells was covered with a layer of agarose gel. The compound, 4',6-dichloroflavan, (1 μg) was dissolved in ethanol, and applied to the lids of the petri dishes. When the ethanol had evaporated, leaving the compound spread over the inside of the lids, these were replaced on the petri dishes. Sufficient compound penetrated the agarose layer to cause total inhibition of plaque formation.

EXAMPLES 105 TO 166

The following compositions were prepared according to the techniques known in the art of pharmacy.

EXAMPLE 105

An inhalant for us in an insufflator was prepared from the following ingredients

| | |
|---|---|
| 4',6-dichloroflavan | 0.6 g |
| isopropylmyristate | 10 g |
| Tween 80 | 0.5 g |
| Span 80 | 0.5 g |
| methyl-p-hydroxy-benzoic acid | 0.1 g |
| Water to | 100 ml |

EXAMPLE 106

A suspension for use as nose drops was prepared from the following ingredients

| | |
|---|---|
| 4',6-dichloroflavan | 0.6 g |
| Keltrol | 0.1 g |
| Sodium Chloride | 0.5 g |
| Sodium lauryl sulphate | 0.1 g |
| Methyl-P-hydroxy-benzoic acid | 0.1 g |
| Water to | 100. ml |

EXAMPLE 107

| Capsule 2 | |
|---|---|
| 4',6-dichloroflavan | 6 g |
| Spray-dried lactose | 208 g |
| Maize starch | 20.8 g |
| Polyvinylpyrollidine | 5.2 g |

Gelatin capsules (size 0) were each filled with 500 mg. of the formulation, affording 10 mg. of active ingredient per capsule.

EXAMPLE 108

| Capsule 1 | |
|---|---|
| 4',6-dichloroflavan | 6 g |
| Spray-dried lactose | 300 g. |

Gelatin capsules (size 1) were each filled with 400 mg. of the formulation, affording 10 mg. of the active ingredient per capsule.

EXAMPLE 109

Tablet of 4',6-dichloroflavan

A tablet formulation containing a mixture of 4',6-dichloroflavan (10 mg), lactose (90 mg), maize starch (10 mg) and magnesium stearate (1 mg) is prepared by wet granulation.

EXAMPLES 110 TO 165

Tablet formulations, each containing one of the flavan derivatives of Examples 48 to 102 are prepared by a method exactly analogous to Example.109

EXAMPLE 166

| Oil formulation of 4',6-dichloro flavan | |
|---|---|
| 4'6-dichloroflavan | 1 g. |

-continued

| Oil formulation of 4',6-dichloro flavan | |
|---|---|
| olive oil B.P. | 1 g. |

The compound was dissolved in olive oil for use by oral administration.

EXAMPLE 167

Various flavan derivatives were tested by the plaque reduction test described above and their $ED_{50}$'s against rhinovirus serotype 1B were ascertained

| Flavan derivative | $ED_{50}(\mu M)$ |
|---|---|
| 4',6-dichloro- | 0.0014 |
| 4'-methyl-6-chloro- | 0.0023 |
| 4'-methyl- | 0.0125 |
| 6-methoxyl- | 0.0125 |
| 4'-methoxyl-6-chloro- | 0.013 |
| 2'-methyl- | 0.015 |
| 4'-chloro-7-methyl- | 0.0155 |
| 3',4'-dichloro-6-methyl- | 0.017 |
| 4'-fluoro- | 0.0175 |
| 4'-bromo-6-chloro | 0.021 |
| 4'-bromo- | 0.036 |
| 4'-chloro- | 0.04 |
| 3',4'-dichloro- | 0.04 |
| 4',6-dimethyl- | 0.042 |
| flavan | 0.046 |
| 2',6'-dichloro- | 0.048 |
| 4',7-dichloro- | 0.048 |
| 4'-amino- | 0.05 |
| 6-chloro- | 0.05 |
| 4'-hydroxy- | 0.06 |
| 2',4'-dichloro- | 0.064 |
| 4'-acetoxyl- | 0.067 |
| 4'-methoxyl- | 0.07 |
| 7-chloro- | 0.07 |
| 4'-methyl-7-chloro- | 0.083 |
| 4'-methoxyl-6-methyl- | 0.1 |
| 2'-chloro- | 0.112 |
| 3'-methoxyl- | 0.125 |
| 6-methyl- | 0.15 |
| 4'-N,N—dimethylamino- | 0.265 |
| 3'-chloro- | 0.27 |
| 3'-methyl- | 0.29 |
| 2'-methoxyl- | 0.37 |
| 2'-hydroxyl- | 0.78 |
| 3'-trifluoromethyl | 1.4 |
| 6-bromo-4'-chloro- | 0.005 |
| 4'-chloro-6-cyano | 0.006 |
| 4',6-dibromo- | 0.008 |
| 4',6-cyano | >0.01 |
| 4'-bromo-6-fluoro- | 0.013 |
| 4'-chloro-6-fluoro- | 0.015 |
| 4'-chloro-6-iodo- | 0.015 |
| 6-chloro-4'-fluoro | 0.016 |
| 6-bromo-4'-methyl- | 0.018 |
| 6-bromo- | 0.019 |
| 6-fluoro- | 0.02 |
| 6-bromo-4'-iodo- | 0.021 |
| 4'-fluoro-6-iodo | 0.028 |
| 6-bromo-4'-fluoro | 0.029 |
| 6-chloro-4-(1-methylethyl) | 0.036 |
| 6-cyano- | 0.038 |
| 4',6-diiodo- | 0.043 |
| 4'-chloro-6-ethyl- | 0.052 |
| 6-iodo- | 0.058 |
| 4',6-difluoro- | 0.068 |
| 2'-methoxyl- | 0.07 |
| 4'-bromo-6-iodo | 0.076 |

EXAMPLES 168 TO 176

2'-Hydroxychalcones

The following were prepared by the method of Example 1 from the corresponding aromatic aldehyde and substituted 2-hydroxy acetophenone:

| Example | Chalcone | M. pt (°C.) |
|---|---|---|
| 168 | 5'-chloro-4-fluoro-2'-hydroxy | 183°-185° |
| 169 | 4,5'-difluoro-2-hydroxy | 168°-170° |
| 170 | 4-chloro-5'-fluoro-2'-hydroxy | 176°-178° |
| 171 | 4-bromo-5'fluoro-2'-hydroxy | 180°-183° |
| 172 | 5'-cyano-2'-hydroxy | 196°-198° |
| 173 | 4-chloro-5'-cyano-2'-hydroxy | 248°-251° |
| 174 | 5'-chloro-2',4-dihydroxy | 172°-177° |
| 175 | 4,5'-dicyano-2'-hydroxy | 263°-265° |

EXAMPLES 176 TO 183

2-Hydroxychalcones

The following were prepared by the method of Example 44 from the corresponding substituted acetophenone and substituted salicylaldehyde:

| Example | Chalcone | M. pt (°C.) |
|---|---|---|
| 176 | 5-bromo-4'-fluoro-2-hydroxy | 185° (dec.) |
| 177 | 4',5-dibromo-2-hydroxy | 177°-179° (dec.) |
| 178 | 4'-fluoro-5-iodo-2-hydroxy | 170° (dec.) |
| 179 | 4'-bromo-5-iodo-2-hydroxy | 163°-166° (dec.) |
| 180 | 4'-chloro-5-iodo-2-hydroxy | 155°-160° (dec.) |
| 181 | 2-hydroxy-5-iodo | 163°-164° |
| 182 | 4'-5-diiodo-2-hydroxy | 184°-185° |
| 183 | 5-bromo-2-hydroxy-4'-iodo | 182°-185° (dec.) |

EXAMPLES 184–191

The following flavans were prepared by sodium borohydride reduction of the corresponding 2'-hydroxychalcones of Examples 168 to 175 followed by cyclisation of the intermediate to the [2H]-3-flavene and catalytic hydrogenation of the flavene to flavan using 10% palladium on carbon in acetic acid according to the method of Example 89. The unstable allylic carbinol presumed to be produced from the borohydride reduction was not isolated in a pure state in any case. The flavenes, purified by chromatography, were characterised by their n.m.r. spectra, and the flavans also characterised spectroscopically.

| Example | Flavan | M. pt (°C.) |
|---|---|---|
| 184 | 4'-fluoro-6-chloro | 92°-93° |
| 185 | 4'-6-difluoro | 87°-89° |
| 186 | 4'-chloro-6-fluoro | 115° |
| 187 | 4'-bromo-6-fluoro | 111°-113° |
| 188 | 6-cyano | 111°-113° |
| 189 | 4',6-dicyano | 147°-149° |
| 190 | 4'-chloro-6-cyano | 125°-126° |
| 191 | Cancelled | |

EXAMPLES 192 TO 199

The following flavans were obtained by borohydride reduction of the corresponding 2-hydroxychalcones and cyclisation of the intermediate fully reduced carbinols with p-toluene sulphonic acid in refluxing toluene (cf the method of Example 97). The intermediate carbinols were not fully purified and characterised.

| Example | Flavan | M. pt (°C.) |
|---|---|---|
| 192 | 6-bromo-4'-fluoro | 83°-85° |
| 193 | 4',6-dibromo | 116-117° |
| 194 | 6-iodo-4'-fluoro | 80°-82° |
| 195 | 4'-chloro-6-iodo | 113°-115° |
| 196 | 4'-bromo-6-iodo | 125°-127° |
| 197 | 6-iodo | 71°-72° |
| 198 | 4',6-diiodo | 140°-142° |
| 199 | 6-bromo-4'-iodo | 126°-128° |

We claim:

1. A mono- or di-substituted flavan of formula (IID)

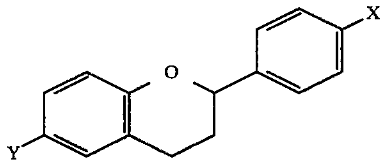

(IID)

wherein either both X and Y represent groups independently selected from amino and lower alkylamino, or one of X and Y represents a group selected from amino and lower alkylamino and the other of X and Y represents a hydrogen atom.

2. A mono- or di-substituted flavan of formula (IID')

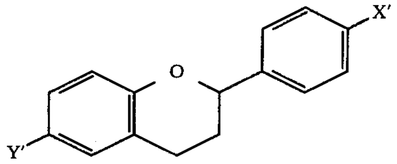

(IID')

wherein either both X' and Y' represent groups independently selected from amino and N,N-dimethylamino or one of X' and Y' represents a group selected from amino and N,N-dimethylamino and the other of X' and Y' represents a hydrogen atom.

3. A mono-substituted flavan of formula (IIE)

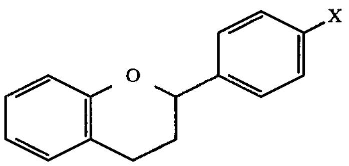

(IIE)

wherein X represents a group selected from amino and lower alkylamino.

4. A mono-substituted flavan of formula (IIE')

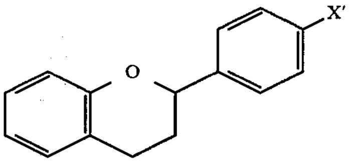

(IIE')

wherein X' represents a group selected from amino and N,N-dimethylamino.

5. 4'-aminoflavan.

6. 4'-N,N-dimethylaminoflavan.

* * * * *